United States Patent [19]
Goldberg

[11] Patent Number: 5,306,724
[45] Date of Patent: Apr. 26, 1994

[54] METHOD FOR PREVENTING AND TREATING ATHEROSCLEROSIS

[75] Inventor: Dennis I. Goldberg, Palatine, Ill.

[73] Assignee: Clintec Nutrition Company, Deerfield, Ill.

[21] Appl. No.: 930,183

[22] Filed: Aug. 17, 1992

[51] Int. Cl.$^5$ .................................. A61K 31/425
[52] U.S. Cl. .................................... 514/369; 514/824
[58] Field of Search ............................. 514/369

[56] References Cited

U.S. PATENT DOCUMENTS

| | | | |
|---|---|---|---|
| 4,175,130 | 11/1979 | Yamanaka et al. | 514/369 |
| 4,665,082 | 5/1987 | Meister et al. | 514/369 |
| 4,791,125 | 12/1988 | Clark | 514/369 |
| 4,798,835 | 1/1989 | Krupp et al. | 514/369 |
| 5,002,953 | 3/1991 | Hindley | 514/369 |
| 5,095,027 | 3/1992 | Goldberg et al. | 514/369 |

OTHER PUBLICATIONS

Rosenfeld et al., "Macrophage-Derived Foam Cells Freshly Isolated from Rabbit Atherosclerotic Lesions Degrade Modified Lipoproteins, Promote Oxidation of Low-Density Lipoproteins, and Contain Oxidation-Specific Lipid-Protein Adducts", J. Clin. Invest., vol. 87, pp. 90-99 (1991).
Heinecke et al., "The Role of Sulfur-Containing Amino Acids in Superoxide Production and Modification of Low Density Lipoprotein by Arterial Smooth Muscle Cells", J. Biol. Chem., vol. 262, pp. 10098-10103, 1987.
Parthasarathy, "Oxidation of Low-Density Lipoprotein by Thiol Compounds Leads to its Recognition by the Acetyl LDL Receptor", Biochim. et Biophys. Acta, vol. 917, pp. 337-340, 1987.
Kuzuya et al., Biochem. Biophys. Res. Commun., vol. 163 (3), 1989, pp. 1466-1472 (From Biosis BA88:127635).

Primary Examiner—Frederick E. Waddell
Assistant Examiner—William R. A. Jarvis
Attorney, Agent, or Firm—Hill, Steadman & Simpson

[57] ABSTRACT

The present invention provides a method for treating atherosclerosis. The method includes the step of administering to a patient having atherosclerosis, a noncysteine, non-thiol composition that will stimulate the intracellular synthesis of glutathione. In an embodiment, the non-cysteine, non-thiol composition is L-2-oxothiazolidine-4-carboxylate. In an embodiment of the present invention, the present invention provides a method for preventing atherosclerotic lesions in a patient at risk of same. Furthermore, the present invention provides a method for preventing re-stenosis in a patient undergoing an invasive procedure to treat atherosclerosis.

14 Claims, No Drawings

METHOD FOR PREVENTING AND TREATING ATHEROSCLEROSIS

BACKGROUND OF THE INVENTION

The present invention relates generally to the treatment of cardiovascular disease. More specifically, the present invention relates to treatment of atherosclerosis.

Cardiovascular disease is the leading cause of death in the United States. In the United States, of a population of 226.5 million in 1980, 551,400 died of ischemic heart disease and 169,500 died of cerebrovascular causes related to arterial disease. See, Merck Manual, Fifteenth Edition, pp. 386.

Atherosclerosis is a form of arteriosclerosis marked by the formation of atheromas. The disease causes the lumen of an artery to become narrowed or blocked (occluded). The atheroma obstructs circulation by protruding into the arterial lumen. The narrowing of the artery restricts blood flow to the organ that is nourished by the artery. The reduced blood flow results in the deterioration of the organ to the point wherein the organ can be permanently damaged unless the blockage of blood flow is removed. When an artery that serves the heart is narrowed or blocked, this pathological process results in a heart attack.

The relationship between hypercholesterolemia, abnormal lipoprotein profiles, and atherogenesis has been well defined. More recently, oxidative modification of lipoproteins, lipoprotein (a), and induction of cytokines and growth factors have been implicated as important factors in the initiation and progression of atherosclerotic plaques.

Lipid peroxidation is one of the deleterious effects of oxidative stress. Peroxidation of the unsaturated lipid moieties of lipoproteins results in a sequelae of events yielding oxidatively modified lipoproteins and macrophage derived foam cells. These cells, which constitute a significant portion of the cells within atherosclerotic lesions, phagocytose and degrade oxidatively modified lipoproteins. See, Rosenfeld et al., *Macrophage-derived Foam Cells Freshly Isolated from Rabbit Atherosclerotic Lesions Degrade Modified Lipoproteins, Promote Oxidation of Low-Density Lipoproteins, and Contain Oxidation-specific Lipid-Protein Adducts*, J. Clin. Invest., Vol. 87, pp. 90-99 (1991).

A number of pharmaceutical interventions have been proposed for treating and/or preventing atherosclerosis. Although the logic of attempting to protect against lipoprotein modification and ensuing lipid hydroperoxide generation may be apparent, the role of glutathione as providing antioxidant protection is at best unsettled. Heinecke et al., *The Role of Sulfur-containing Amino Acids in Superoxide Production and Modification of Low Density Lipoprotein by Arterial Smooth Muscle Cells*. J. Biol. Chem., Vol. 262, pp. 10098-10103, 1987, reported that monkey arterial smooth muscle cells produce reactive oxygen species and modify low density lipoprotein by an L-cysteine dependent process. This effect was postulated to involve the production of reduced thiols from the cystine, followed by thiol mediated modification of the lipoprotein.

Parthasarathy, *Oxidation of Low-density Lipoprotein by Thiol Compounds Leads to its Recognition by the Acetyl LDL Receptor*, Biochim. et Biophys. Acta, Vol. 917, pp. 337-340, 1987 also demonstrated that reduced glutathione and other compounds with reduced thiols promote the oxidation of LDL in the absence of cells. This reaction was hypothesized to be the result of thiol reaction with redox metals, generating free radicals which promote modification of LDL. Parthasarathy further notes: "There appears to be some correlation among plasma cholesterol levels, incidence of atherosclerosis, and levels of protein-bound-homocysteine. Cysteine and other thiols, including protein-bound thiols, undergo auto-oxidation in the presence of redox metals, generating peroxide, superoxide anion and hydroxy radicals in addition to thiol-derived free radicals." See pp. 339.

In many cases of atherosclerosis, invasive procedures such as bypass surgery or angioplasty are required to reestablish an occluded lumen to proper diameter.

Due to its intrusive nature, bypass surgery inherently has a number of disadvantages. Accordingly, the popularity of angioplasties has increased dramatically. In the United States in 1989, hundreds of thousands of angioplasties were performed. This number is rapidly increasing. Fortunately, for many patients, angioplasty permanently reopens the previously occluded arteries. However, in approximately 30% of the occluded arteries which are opened by an angioplasty technique, the arteries re-occlude within six months of the procedure. This results in symptoms of cardiac ischemia, such as chest pain, exercise intolerance, and shortness of breath. The patient's risk of disabling or fatal heart attack is markedly increased.

It is believed that re-stenosis in a previously treated segment of an artery is due, at least in part, to the stretch-induced damage of arterial tissue. The response to the damage caused by the inflation of a balloon catheter is an exaggerated healing response that includes proliferation of the endothelial cells.

Likewise, even in bypass surgery there is a danger of re-stenosis in the patient. Bypass grafts in 40% of patients restenose within 5 years of the surgical procedure

SUMMARY OF THE INVENTION

The present invention provides a method of treating atherosclerosis. More specifically, the present invention provides a method of preventing the initiation and/or progression of atherosclerotic lesions. Furthermore, the present invention provides a method for preventing the re-stenosis of coronary vessels following angioplasty or bypass surgery.

To this end, the present invention provides a method for treating atherosclerosis. The method includes the step of administering to a patient having atherosclerosis, a non-cysteine, non-thiol composition that will stimulate the intracellular synthesis of glutathione. In an embodiment, the non-cysteine, non-thiol composition is L-2-oxothiazolidine-4-carboxylate.

In an embodiment of the present invention, the composition is administered enterally.

In an embodiment of the present invention, the composition is administered parenterally.

In an embodiment of the present invention, the present invention provides a method for preventing atherosclerotic lesions in a patient at risk of same. The method comprises administering to a patient at risk of atherosclerotic lesions a therapeutically effective amount of a non-cysteine, non-thiol product that stimulates the intracellular synthesis of glutathione.

Furthermore, the present invention provides a method for preventing re-stenosis in a patient undergoing an invasive procedure to treat atherosclerosis. The method comprises the step of administering to the patient prior to and after the invasive procedure, a therapeutically effective amount of a non-thiol, non-cysteine intracellular glutathione stimulator.

In an embodiment of the method, the invasive procedure is bypass surgery.

In an embodiment of the method, the invasive procedure is angioplasty.

Additional features and advantages of the present invention are described in, and will be apparent from, the detailed description of the presently preferred embodiments.

DETAILED DESCRIPTION OF THE PRESENTLY PREFERRED EMBODIMENTS

The present invention relates to a method of treating atherosclerosis in a patient having same. Furthermore, the present invention relates to a method for preventing atherosclerotic lesions in a patient at risk of same. Still further, the present invention provides a method of preventing re-stenosis in a patient who has undergone an invasive procedure such as angioplasty or bypass surgery.

To this end, the present invention provides a method of treating atherosclerosis comprising the step of administering to a patient a non-thiol, non-cysteine, intracellular glutathione stimulator.

As used herein, "non-cysteine" means that the composition does not include cysteine. Accordingly, compositions excluded from this definition, include, cysteine and n-acetylcysteine.

Of course, thiols are sulfur analogs of alcohols and phenols. As used herein, "non-thiol" means that the compound does not contain such a sulfur analog.

Atherogenesis is in many ways an inflammatory reaction in the arterial wall. The chain reaction of lipid peroxidation can be blocked by the action of phospholipid hydroperoxide glutathione peroxidase, a second selenoperoxidase, similar to the classic glutathione peroxidase, but which acts upon membrane lipid and cholesterol hydroperoxides. Since glutathione peroxidase is one of the primary defense mechanisms against lipid hydroperoxides, stimulation of intracellular glutathione synthesis may prevent the initiation, or break the cycle, of lipid peroxidation believed to be the cause of oxidative lipoprotein modification. This thereby prevents one of the initiating events in atherosclerosis formation.

Vascular endothelial cells, which form an impermeable barrier to lipoprotein infiltration to the subendothelial space, can be damaged by membrane lipid peroxidation. This damage, which can be caused by reactive oxygen species generated within endothelial cells, in lipoproteins, or generated by neutrophils, can lead to further damage of the arterial wall by promoting the adhesion and activation of neutrophils and platelet aggregation.

Adhesion of circulating monocytes and lymphocytes to the endothelial lining is one of the earliest detectable events in animal models of experimental atherosclerosis. The cells subsequently become engorged with lipids and begin to secrete cytokines and growth factors which exacerbate the injury. The inflammatory process is promoted by cytokine activation of nuclear transcription factor kB (NF-kB). This transcription factor is known to control the expression of a number of genes that code for cytokines and other proteins involved in the inflammatory process.

In fact, most inflammatory agents activate this transcription factor, which then induces genes that contribute to local inflammatory reactions and lymphocyte activation. Among the proteins induced by inflammation are a variety of adhesion molecules for polymorphonuclear and mononuclear leukocytes. A rabbit homolog of the human adhesion molecule VCAM-1 has recently been identified in the aortic endothelium that covers early foam cell lesions.

Intracellular free radicals and hydrogen peroxides may serve as second messengers, transducing the cytokine signal to activate NF-kB. The activation of NF-kB by a variety of pro-inflammatory cytokines, including interleukin-1. Lipopolysaccharide, lectin, TNF-α, phorbol ester and calcium ionophore, can be blocked by thiol containing compounds. Elevation of intracellular glutathione levels has been demonstrated to prevent the induction of HIV replication by NF-kB. The inventor believes that this data supports the hypothesis that maintaining intracellular glutathione levels may prevent the induction of proinflammatory genes and thereby slow or prevent the initiation and expansion of atherosclerotic lesions.

Although the art would suggest to one that the role of glutathione as a treatment of atherosclerosis is, at best, unclear and perhaps contraindicated, the inventor has discovered how beneficial effects of glutathione can be used without the disadvantages described supra.

Since the elevation of intracellular glutathione may be beneficial in preventing atherosclerosis, while extracellular thiols may exacerbate lipoprotein modification due to a thiol/redox reaction generation of free radicals, pursuant to the method of the present invention intracellular glutathione synthesis is stimulated by a non-cysteine, non-thiol precursor.

An example of such an agent is L-2-oxothiazolidine-4-carboxylate. Likewise, other non-cysteine, non-thiol intracellular stimulators can be used, e.g. other thiazolidine-4-carboxylate analogs.

L-2-oxothiazolidine-4-carboxylate, in vivo, is subjected to the action of 5-oxo-L-prolinase in the presence of adenosine triphosphate to produce S-carboxyl cysteine. S-carboxyl cysteine is then decarboxylated to produce cysteine. Cysteine is then metabolized to produce glutathione. See, U.S. Pat. Nos.: 4,335,210; 4,434,158; 4,438,124; 4,647,571; and 4,665,082, the disclosures of which are incorporated herein by reference. Due to the intracellular synthesis of both the cysteine and the glutathione the disadvantages noted in the art with respect to cysteine and thiols is not a concern.

An example of a composition that can be administered to the patient is 3% w:v L-2-oxothiazolidine-4-carboxylate, pH 7.0 in phosphate buffer. The composition can be administered at a dose of 10 to 100 mg/kg/day. The composition can be administered alone or with nutrients such as an amino acid solution.

A second example of a composition that can be administered to the patient is a capsule containing 500 mg of L-2-oxothiazolidine-4-carboxylic acid, 167.4 mg cornstarch, 64 mg lactose and 3.6 mg ascorbic acid. The composition can be administered at a dose of one to three capsules one to three times per day.

A third example of a composition that can be administered to the patient is a lyophilized sachet containing a 1 to 5 gram cake of L-2-oxothiazolidine-4-carboxylic acid which is subsequently dissolved in orange, apple, grapefruit, or other juices. The composition is taken orally one to three times per day.

The composition of the present invention can be administered to a patient having atherosclerosis as a treatment. Likewise, the present invention can be used to prevent the formation of atherosclerotic lesions in a patient likely to suffer same. Furthermore, the present invention can be used to prevent re-stenosis in a patient who has undergone an invasive treatment, i.e. bypass surgery or a angioplasty, for atherosclerosis.

By way of example, and not limitation, contemplative examples of the present invention will now be given.

EXAMPLE NO. 1

A 49 year old female with non-insulin dependent diabetes mellitus reported incidence of angina pectoris and shortness of breath to her physician. Plasma lipid peroxide level, measured as malondialdehyde, was 5.3 nmol/ml as compared to 3.7 nmol/ml in normal subjects. The level of autoantibodies to malondialdehyde-modified low density lipoproteins was determined by solid-phase radioimmunoassay. The malondialdehyde-LDL titer was 2.93 vs. 2.06 for normal subjects. Positron Emission Tomography (PET) scan revealed a significant decrement in coronary flow reserve through the left anterior descending coronary artery.

The patient was placed on a sugar free diet to control glucose levels and given 1 gram of L-2-oxothiazolidine-4-carboxylic acid (2 capsules with meals) t.i.d. The incidence of angina diminished within 2 weeks. After two months plasma malondialdehyde was down to 3.3 nmol/ml, and the autoantibody titer had declined to 2.24.

The patient was maintained on L-2-oxothiazolidine-4-carboxylic acid for 1 year. Repeat PET scan indicated a definite improvement in coronary flow reserve.

EXAMPLE NO. 2

A 43 year old male with total cholesterol level of 270 complained of severe chest pain and shortness of breath. Coronary arteriogram demonstrated 90% occlusion of the right circumflex artery. The patient was scheduled for angioplasty.

The patient was administered 1.5 g of L-2-oxothiazolidine-4-carboxylic acid t.i.d. for 48 hours prior to the angioplasty. During the procedure, the occluded artery was perfused with a 3% L-2-oxothiazolidine-4-carboxylic acid solution in phosphate buffered saline through the lumen of the balloon catheter.

Intravenous L-2-oxothiazolidine-4-carboxylic acid solution (5% in 5% dextrose) was administered at a dose of 30 mg/kg every 8 hours for 24 hours. The patient was then administered 1 gram of L-2-oxothiazolidine-4carboxylic acid t.i.d. for 30 days. Follow-up arteriography demonstrated that the treated artery was patent 1 year after the surgical event.

EXAMPLE NO. 3

A 55 year old man suffered a myocardial infarction. Plasma cholesterol levels were 240 and plasma lipid peroxide levels were 4.80 nmol of malondialdehyde/ml. Coronary arteriography indicated three vessel disease and the patient was scheduled for coronary bypass surgery.

Prior to surgery, the patient was administered a 5% L-2-oxothiazolidine-4-carboxylic acid solution in lactated Ringer's solution, 60 mg/kg every eight hours. During surgery, the patient received a sold cardioplegia solution containing 2.5 mM L-2-oxothiazolidine-4-carboxylic acid.

During recovery from surgery, the patient continued to receive the 5% L-2-oxothiazolidine-4-carboxylic acid solution in lactated Ringer's solution, 60 mg/kg every eight hours, for 48 hours. Plasma malondialdehyde declined to 3.20 nmol/ml at the end of 48 hours. The intravenous solution was removed and oral L-2-oxothiazolidine-4-carboxylic acid was administered, 1 g t.i.d. Oral treatments were continued for 60 days post surgery, then decreased to 0.5 g t.i.d. for the next year.

Follow up angiography revealed less than 20% restenosis of any of the surgery treated vessels at one year. Plasma lipid peroxides remained below 3.3 nmol/ml, and the titer of autoantibodies to malondialdehydemodified LDL, as measured by solid phase radioimmunoassay, remained 2.0. The patient was free of angina at a two year follow up visit.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for treating atherosclerosis comprising the step of administering to a patient having atherosclerosis a therapeutically effective amount of L-2-oxothiazolidine-4-carboxylate that stimulates the intracellular synthesis of glutathione.

2. The method of claim 1 wherein the product is administered enterally.

3. The method of claim 1 wherein the product is administered parenterally.

4. The method of claim 1 wherein the product is administered with an amino acid solution.

5. A method for preventing atherosclerotic lesions in a patient at risk of same comprising the steps of administering to the patient a therapeutically effective amount of a L-2-oxothiazolidine-4-carboxylate product that stimulates the intracellular synthesis of glutathione.

6. The method of claim 5 wherein the product is administered enterally.

7. The method of claim 5 wherein the product is administered parenterally.

8. The method of claim 5 wherein the product is administered with an amino acid solution.

9. A method for preventing re-stenosis in a patient undergoing an invasive procedure to treat atherosclerosis comprising the step of administering to the patient prior to and after the invasive procedure a therapeutically effective amount of L-2-oxothiazolidine-4-carboxylate.

10. The method of claim 9 wherein the product is administered enterally.

11. The method of claim 9 wherein the product is administered parenterally.

12. The method of claim 9 wherein the product is administered with an amino acid solution.

13. The method of claim 9 wherein the invasive procedure is bypass surgery.

14. The method of claim 9 wherein the invasive procedure is angioplasty.

* * * * *